United States Patent

Yamada et al.

[11] Patent Number: 5,149,793
[45] Date of Patent: Sep. 22, 1992

[54] EXO-3',4'-O-BENZYLIDENE-3''-DEMETHYL-CHARTREUSIN AND ITS SALTS

[75] Inventors: Nobutoshi Yamada; Hideo Sugi; Sadanori Mizukoshi; Kenji Kon; Taiji Katayama, all of Kusatsu, Japan

[73] Assignee: Ishihara Sangyo Kaisha, Ltd., Osaka, Japan

[21] Appl. No.: 471,428

[22] Filed: Jan. 29, 1990

[30] Foreign Application Priority Data

Jan. 30, 1989 [JP] Japan ................................. 1-19957
Apr. 5, 1989 [JP] Japan ................................. 1-86588

[51] Int. Cl.$^5$ ..................... C07H 17/04; C07H 15/24; A61K 31/71
[52] U.S. Cl. .................................. 536/16.8; 536/18.1; 536/17.2; 536/4.1
[58] Field of Search .................. 536/18.1, 17.5, 17.2, 536/17.4, 17.3, 16.8; 514/17.4, 34

[56] References Cited

U.S. PATENT DOCUMENTS 4,518,589  5/1985  Konishi et al. ..................... 536/17.2
4,760,136  7/1988  Mori et al. ......................... 536/17.2
4,927,919  5/1990  Yamada et al. ..................... 536/17.2

FOREIGN PATENT DOCUMENTS 2-59596  2/1990  Japan .

OTHER PUBLICATIONS

Konishi et al., The Journal of Antibiotics, vol. XXXIX (6), 784–791 (1986).
J-Patrick McGovren et al., Cancer Research, 37, 1666–1672 (1977).
Takai et al., J. Med. Chem., 23, 549–553 (1980).
Leach, B. E., et al., (1953) [J. Am. Chem. Soc., 75 4011–4012 (1953)].

Primary Examiner—Ronald W. Griffin
Assistant Examiner—Louise Leary
Attorney, Agent, or Firm—Cushman, Darby & Cushman

[57] ABSTRACT

Exo-3',4'-O-benzylidene-3''-dimethylchartreusin (exo-BDMC) or its salts and 3''-demethylchartreusin (3''-DMC) or its salts are provided according to the present invention. Exo-BDMC and its salts are useful for antitumorous agents and antibacterial agents. 3''-DMC and its salts are useful as starting materials for producing exo-BDMC.

3 Claims, No Drawings

EXO-3′,4′-O-BENZYLIDENE-3″-DEMETHYL-CHARTREUSIN AND ITS SALTS

The present invention relates to novel exo-3′,4′-O-benzylidene-3″-demethylchartreusin (hereinafter referred to as exo-BDMC) represented by the structural formula (I) or its salts, and a process for producing exo-BDMC. The present invention also relates to an antitumorous agent and an antibacterial agent both containing exo-BDMC or its salt(s).

The present invention, further, relates to novel 3″-demethylchartreusin (hereinafter referred to as 3″-DMC) represented by the structural formula (II) or its salts which are useful as starting materials for producing exo-BDMC, and which have antitumorous and antibacterial activities in themselves.

As already known, chartreusin can be obtained through culture of Streptomyces chartreusis, and has antibacterial and antitumorous activities. Exo-3′,4′-O-benzylidenechartreusin as an intermediate of exo-3′,4′-O-benzylidenechartreusin derivatives is also disclosed in U.S. Pat. No. 4,760,136.

The present inventors have found through studies on modification of chartreusin obtained through the culture of *Streptomyces chartreusis* that novel 3″-DMC can be obtained as a by-product through culture of *Streptomyces chartreusis,* and that 3″-DMC has antitumorous and antibacterial activities.

Meanwhile, the present inventors have also confirmed through studies on decomposition and metabolism of exo-3′,4′-O-benzylidenechartreusin derivatives in the bodies of mice that exo-BDMC exists in the excreta of mice. The present inventors have further attempted organic syntheses of exo-BDMC and found that this compound can be derived from the abovementioned 3″-DMC and has antitumorous and antibacterial activities.

The present invention has been completed as a result.

The present invention relates to exo-3′,4′-O-benzylidene-3″-demethylchartreusin or its salts. The present invention also relates to a process for producing exo-3′,4′-O-benzylidene-3″-demethylchartreusin. The present invention further relates to 3″-demethylchartreusin or its salts.

More specifically, the present invention provides exo-BDMC represented by the following structural formula (I) or its salts, and a process for producing exo-BDMC from 3″-DMC as a starting material as well as an antitumorous agent and an antibacterial agent both containing exo-BDMC or its salts.

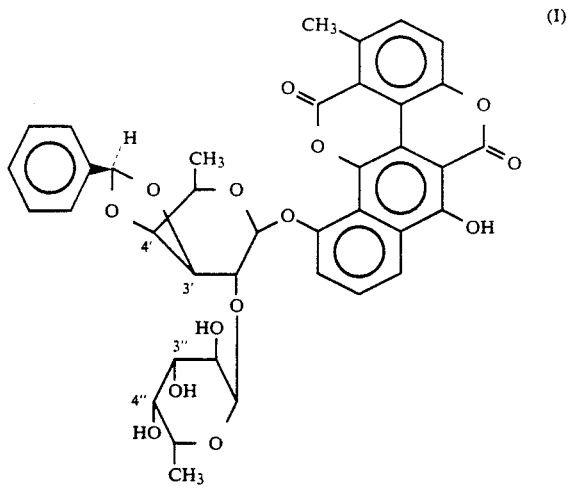

An object of the present invention is to provide exo-BDMC or its salts and a process for producing the same.

Another object of the present invention is to provide 3″-DMC.

Other objects and advantages of the invention will become apparent from the following description.

Exo-3′,4′-O-benzylidenechartreusin (hereinafter referred to as exo-BC), which is a known compound, has a methoxy group at the 3″-position of a sugar (D-digitalose) moiety thereof, whereas an exo-BDMC according to the present invention has a hydroxyl group at the 3″- position.

Salts of exo-BDMC according to the present invention include all physiologically acceptable salts, specific examples of which include alkali metal salts such as sodium salt, potassium salt and the like, alkaline earth metal salts such as calcium salt, magnesium salt and the like and salts of amines such as monoalkylamines, dialkylamines and the like.

A description is now made of a process for producing exo-BDMC according to the present invention.

3″-DMC is used as a starting material for producing exo-BDMC and represented by the following structural formula (II).

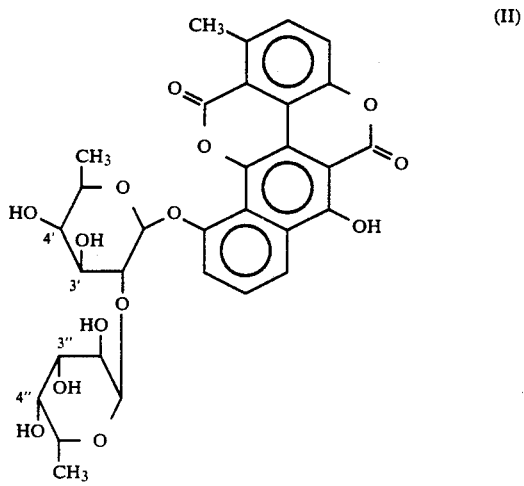

3"-DMC is a compound having a hydroxyl group in place of the methyl group at the 3"-position of a sugar (D-digitalose) moiety of chartreusin.

3"-DMC can be converted into its salts. As salts of 3"-DMC, mention may be made of those corresponding to the salts of exo-BDMC described above.

First, 3"-DMC is reacted with benzaldehyde or benzaldehyde dimethylacetal in a neutral solvent in the conjoint presence of an acid catalyst and molecular sieves to prepare a mixture of several benzylidene-3"-DMCs.

The foregoing reaction may be effected according to a method as disclosed in U.S. Pat. No. 4,760,136 or an analogous method. However, a description will be made of the above-mentioned methods.

An amount of benzaldehyde or benzaldehyde dimethylacetal to be used in the foregoing reaction may usually be 1 to 5 moles per mole of 3"-DMC.

Examples of the neutral solvent include chloroform, benzene, toluene, ethyl acetate, and dimethylformamide. An amount of the neutral solvent to be used in the reaction may usually be 20 to 50 ml per millimole of 3"-DMC.

Examples of the acid catalyst include sulfonic acids such as camphorsulfonic acid, p-toluenesulfonic acid and the like, mineral acids such as hydrochloric acid and the like, and Lewis acids such as zinc chloride and the like. An amount of the acid catalyst to be used in the reaction may usually be 0.1 to 2 moles per mole of 3"-DMC.

Examples of the molecular sieves include molecular sieves 4A, molecular sieves 5A and the like. An amount of the molecular sieves to be used in the reaction may usually be 1 to 4 g per millimole of 3"-DMC.

The reaction may usually be effected at a temperature of 0° to 60° C. for 0.5 to 48 hours.

The mixture of benzylidene-3"-DMCs obtained as a result of the foregoing reaction may include up to eight compounds, namely four isomers of monobenzylidene-3"-DMC and four isomers of dibenzylidene-3"-DMC, because benzylidene has a possibility of being bonded to the 3'- and 4'-positions of a sugar moiety of 3"-DMC and the 3"- and 4"-positions of another sugar moiety of 3"-DMC. The ratio of the amount of monobenzylidene-3"-DMCs to that of dibenzylidene-3"-DMCs as well as the ratio of the isomers thereof depends upon reaction conditions chosen.

Subsequently, the mixture of several benzylidene-3"-DMCs formed by the aforementioned reaction is subjected to selective solvolysis to decompose benzylidene-3"-DMCs other than exo-BDMC. Thus, only exo-BDMC is obtained.

After the removal of the molecular sieves from the solution containing the mixture of several benzylidene-3"-DMCs formed by the aforementioned reaction, the above-mentioned selective solvolysis can be allowed to proceed by adding an alcohol such as methanol to the solution to covert benzylidene-3"-DMCs other than exo-BDMC into 3"-DMC. An amount of the alcohol to be used in the selective solvolysis may be usually 0.1 to 2 ml per millimole of the mixture of several benzylidene-3"-DMCs. The selective solvolysis reaction may be usually effected at a temperature of 0° to 60° C. for 0.5 to 5 hours. Subsequently, the reaction mixture obtained after the selective solvolysis is admixed with a base such as pyridine to neutralize the reaction system. The resulting neutralized solution is concentrated under reduced pressure. Thereafter, the concentrated solution is subjected to a customary purification procedure such as silica gel column chromatography to isolate exo-BDMC. The isolated exo-BDMC may be further purified according to a customary recrystallization procedure to obtain exo-BDMC having a higher purity. Exo-BDMC thus obtained can be converted into a salt thereof according to a customary method.

A description is now made of the preparation of 3"-DMC as a starting material of exo-BDMC according to the present invention.

First, *Streptomyces chartreusis* as a productive microorganism is cultured in a medium to accumulate 3"-DMC in the culture broth. As the streptomyces chartreusis which is used in the present invention, any customary available ones are usable, examples of which include Streptomyces chartreusis IFO-12753. Employable culture methods include a wide variety of known actinomycetes culture methods and variants thereof. For example, the culture may be carried out in a liquid medium according to a submerged culture method. Every kind of medium containing nutrient sources capable of being utilized by a strain of Streptomyces chartreusis is usable. Known substances as used in the customary actinomycetes culture can be used as the nutrient sources.

As carbon sources, carbohydrates such as glycerin, glucose, lactose, molasses, and starch can be used. Examples of usable nitrogen sources include urea, ammonium sulfate, nitrates, meat extract, yeast extract, corn steep liquor, peptone, casein, and soybean powder. Examples of usable inorganic salts include sodium chloride, phosphates, potassium chloride, calcium carbonate, and magnesium sulfate. Additionally, other various growth factors, defoaming agents, etc. can optionally be used.

The culture may be carried out in the medium having a pH value of 5 to 9, preferably 6 to 7, under aerobic conditions at a temperature of generally 20° to 35° C., preferably 25° to 30° C. In this case, the production of 3"-DMC is maximized after 4 to 10 days, desirably 6 to 8 days, of culture according to either jar-fermentor culture or shake culture.

Subsequently, 3"-DMC is collected from the culture broth containing 3"-DMC accumulated therein The collection of 3"-DMC can be made using any one of various customary procedures of isolating an antibiotic from a culture broth resulting from culture of a microorganism and purifying the isolated antibiotic. For example, the culture broth containing 3"-DMC accumulated therein is subjected to centrifugal separation or filtration to effect the solid-liquid separation thereof, followed by extraction of 3"-DMC from the resulting supernatant liquid or the resulting filtrate as well as from the separated cell bodies to obtain an extract, which is then subjected to a customary purification procedure to obtain pure 3"-DMC.

Exo-BDMC or its salts according to the present invention exhibit activities against cells of experimental tumors of mice and the like, such as P-388 leukemia, L-1210 leukemia, B-16 melanoma, M-5076 sarcoma, Colon 26, and Lewis lung carcinoma, thus proving that they are useful as antitumorous agents. They also exhibit a capacity of strongly inhibiting growth of either Gram-positive bacteria or Gram-negative bacteria, thus proving that they are useful as antibacterial agents, disinfectants for medical and other appliances, therapeutic agents for human and animal microbisms, etc.

Exo-BDMC or its salts according to the present invention (hereinafter referred to as compound of the present invention) may be used for a serviceable pharmaceutical preparation according to any one of various methods as employed in the case of medicinal antibiotics. For example, the compound of the present invention is admixed with an inactive diluent, and the resulting mixture is formed into one of various dosage forms such as powders, tablets, troches, capsules, suspensions, syrups, creams, ointments, injections, and suppositories.

A description will be made of a dose of the compound of the present invention and a route of administration thereof. In the case of animals, the compound of the present invention may be administered in the form of an injection such as an intraperitoneal, intravenous or local injection, or an oral drug. In the case of human beings, the compound of the present invention may be administered in the form of an injection such as an intravascular (intravenous or intraarterial) or local injection, an oral drug, a suppository, or the like. While giving consideration to various conditions and the results of animal experiments, the compound of the present invention may be administered either continuously or intermittently in so far as the total dose thereof does not exceed a certain level. However, the dose may, of course, be properly varied depending on an administration route, conditions of a patient or an animal to be treated (for example, age, body weight, sex, sensitivity, and food), intervals between operations of administration, kinds of drugs used in combination with the compound of the present invention, and severity of a disease. An optimum dose and a frequency of administration should be determined by medical specialists.

Examples of biological preparation and synthetic preparation of exo-BDMC according to the present invention and Test Examples are explained below, but they should not be construed as limiting the scope of the present invention.

Example of biological preparation of exo-BDMC according to the present invention is first described.

EXAMPLE OF BIOLOGICAL PREPARATION

Exo-6-O-(N-trifluoroacetyl-$\beta$-aminoisobutyryl)-3',4'-O-benzylidenechartreusin was intravenously injected in a dose of 40 mg/kg into 160 DDY mice. 300 g of feces excreted within 24 hours after the intravenous injection were collected and ground down in a mortar. 1 liter of a mixed solvent (methanol:chloroform=1:1 in volume ratio) was added to the ground-down feces. The resulting mixture was stirred at 60° C. for 30 minutes to effect extraction, followed by separation of insolubles by filtration. The separated insolubles were admixed with 700 ml of the same mixed solvent as mentioned above to effect extraction again. The two resulting extracts were put together and concentrated under reduced pressure to obtain 9 g of crude exo-BDMC. The crude exo-BDMC was subjected to a purification operation by silica gel column chromatography (developing solvent: chloroform+methanol). The above-mentioned purification operation was repeated. An exo-BDMC-containing fraction obtained by the foregoing purification procedure was concentrated and then recrystallized from a mixed solvent (chloroform:methanol:ethyl acetate=2:1:1 in volume ratio) to obtain 50 mg of exo-BDMC.

NMR data on this exo-BDMC are as follows:
NMR (400 MHz, $\delta$ values, in DMSO-$d_6$)
1.00 (3H, d, J=6.4 Hz, 5"—CH$_3$)
1.33 (3H, d, J=6.4 Hz, 5'—CH$_3$)
2.84 (3H, s, Ar—CH$_3$)
4.00–5.54 (10H, sugar proton)
6.16 (1H, s, benzylidene proton)
7.42–8.17 (10H, aromatic proton)
11.59 (1H, s, 6—OH)

Additionally stated, the administered drug was in the form of a suspension prepared by dissolving 200 mg of the test compound in 2.5 ml of dimethylacetamide, adding a surfactant "Tween-80" (trademark of polyoxyethylene sorbitan mono-oleate manufactured by Atlas Co., Ltd.) in an amount of 5% based on the total volume of the suspension to the resulting solution and suspending the resulting mixture in 45 ml of physiological saline.

Next, Example of synthetic preparation of exo-BDMC according to the present invention is specifically described.

Example of Synthetic Preparation (Preparation of 3"-DMC as starting material)

(1) Culture 15 ml of a liquid medium was pipetted into a 50 ml test tube from 1 liter of the liquid medium adjusted to a pH of 7.0 and containing 40 g of lactose, 20 g of a soybean powder, 20 g of a corn steep liquor and 5 g of calcium carbonate, and sterilized according to a customary method. Spores of *Streptomyces chartreusis* IFO-12753 were inoculated in the liquid medium in the test tube and cultured at 28° C. for 3 days according to shake culture to obtain a first inoculum. The first inoculum was inoculated in 500 ml of the same liquid medium as mentioned above, which was placed in a 2 liter flask, and cultured at 28° C for 3 days according to shake culture to obtain a second inoculum. 35 liters of the liquid medium having the same composition as mentioned above was placed in a 50 liter jar fermentor and sterilized according to the customary method, followed by inoculation therein of 1 liter of the second inoculum. Culture of the second inoculum was carried out with a stirrer being rotated at 250 rpm at an air flow rate of 35 liters/minute at a culture temperature of 28° C. for 7 days.

(2) Extraction 70 liters of a culture broth obtained using the same procedure as in the foregoing culture step (1) was adjusted to a pH of 5.5 to 6.0, admixed with 7 kg of sodium chloride to effect salting-out, and subjected to two repeated operations of centrifugal separation by means of a Scharples type centrifuge to separate about 15 kg, on a wet basis, of cell bodies from the mixture. 30 liters of a mixed solvent (chloroform:methanol=2:1 in volume ratio) was added to the cell bodies to effect extraction. This extraction procedure was repeated. The resulting extract layer was concentrated under reduced pressure and admixed with methanol. The resulting mixture was stirred at 50° to 60° C. for 15 minutes and then allowed to stand at 4° C. for one night. Subsequently, the resulting solution was filtered to separate therefrom solid matter, which was then washed with a mixed solvent (ether:hexane=1:3 in volume ratio) and dried to obtain about 10 g of a crude powder.

(3) Purification 10 g of the crude powder obtained in the foregoing extraction step (2) was dissolved in 1 liter of chloroform heated at 60° C. The resulting solution was subjected to several operations of silica gel chromatography to isolate therefrom 300 mg of 3''-DMC having a melting point of 258° to 260° C.

NMR data on this 3''-DMC as a starting material of exo-BDMC according to the present invention are as follows:

NMR (400 MHz, δ values, in DMSO-d$_6$)
0.89 (3H, d, J=6 Hz, 5''—CH$_3$)
1.15 (3H, d, J=6.8 Hz, 5'—CH$_3$)
2.77 (3H, s, Ar—CH$_3$)
3.86–5.37 (10H, sugar proton)
7.46–8.25 (5H, aromatic proton)
11.50 (1H, s, 6—OH)

(Preparation of exo-BDMC)

(1) Reaction for Preparation of Benzylidene Derivatives 1 g of 3''-DMC prepared according to the foregoing process was dissolved in 48 ml of anhydrous chloroform to prepare a solution, then admixed with 1.2 g of benzaldehyde dimethylacetal, 2 g of molecular sieves 5A 1/16 (manufactured by Nakarai Kagaku K.K.) and 380 mg of D-10-camphorsulfonic acid and reacted at room temperature for 45 minutes.

After the completion of the reaction, the reaction mixture was filtered to remove the molecular sieves therefrom. Thus, a solution of several benzylidene-3''-DMCs was obtained.

(2) Selective Solvolysis, Neutralization, and Purification 0.6 ml of methanol was added to the solution of several benzylidene-3''-DMCs obtained in the foregoing step (1), followed by a reaction at room temperature for 45 minutes.

After the completion of the reaction, pyridine was added to the reaction mixture to neutralize the mixture. The resulting neutralized solution was condensed under reduced pressure and subjected to a purification operation by silica gel column chromatography (developing solvent: chloroform+methanol). The foregoing purification operation was repeated. A fraction containing the desired product and obtained through the above-mentioned purification operation was condensed and then recrystallized from a mixed solvent (chloroform:methanol:ethyl acetate=2:1:1 in volume ratio) to obtain 216 mg of exo-BDMC having a melting point of 174° to 177° C.

NMR data on this exo-BDMC are as follows:
NMR (400 MHz, δ values, in DMSO-d$_6$)
1.00 (3H, d, J=6.8 Hz, 5''—CH$_3$)
1.33 (3H, d, J=6.4 Hz, 5'—CH$_3$)
2.84 (3H, s, Ar—CH$_3$)
4.00–5.54 (10H, sugar proton)
6.16 (1H, s, benzylidene proton)
7.42–8.17 (10H, aromatic proton)
11.59 (1H, s, 6—OH)

Next, a description is made of Test Examples respectively concerning the antitumorous and antibacterial activities of exo-BDMC according to the present invention.

TEST EXAMPLE 1 (Antitumorous Activity)

B-16 melanoma cells were suspended in RPMI 1640 medium containing 5% fetal bovine serum in a concentration of $4 \times 10^4$ cells/ml. The resulting suspension was placed in the 12 wells (1 ml/well) of a plate-cum-wells, wherein preliminary incubation was then carried out for 24 hours. A test drug was dissolved in a mixture of dimethyl sulfoxide and a culture medium of 5% serum - RPMI 1640 (1:3 in volume ratio). Thus, drug solutions having various respective drug concentrations were prepared. 20 μl each of these drug solutions were respectively added to the wells of the plate. The resulting drug-added suspensions were subjected to incubation at 37° C. for 1 hour. Subsequently, the incubated medium were removed from the respective wells, which were then washed once with the same culture medium as mentioned above. Thereafter, the same culture medium as mentioned above was freshly placed in each of the wells of the plate, followed by incubation at 37° C. for 48 hours.

The number of cells in each well was counted according to a customary method using a Coulter counter.

The foregoing procedure was followed using each of test drugs as listed in the following Table 1. The values of growth control rate in the members of each drug-treated group, which members corresponding to the respective wells of the plate were culture broths respectively treated with drug solutions having various respective drug concentrations, were calculated by comparison with the growth rate of the drug-untreated group. The inhibitory concentration of each test drug in which the growth control rate was 50% (IC$_{50}$) was calculated from the above-calculated values of growth control rate. The results are shown in the following Table 1.

TABLE 1

| Test Drug | | IC$_{50}$ (μg/ml) |
|---|---|---|
| Plots Using Present Invention | exo-BDMC | 0.9 |
| Plots Using Comparative Drug | chartreusin | 9.2 |
| | 3''-DMC | 11.0 |
| | exo-BC | 2.1 |

TEST EXAMPLE 2 (Antibacterial Activities)

The minimum inhibitory concentrations (MIC) of exo-BDMC against growth of various microorganisms were examined according to an agar dilution method. The results are shown in the following Table 2.

TABLE 2

| Microorganism | MIC (ppm) |
|---|---|
| *Bacillus subtilis* PCI 219 | 1.56 |
| *Staphylococcus aureus* 209P | 3.13 |
| *Bacillus megaterium* IFO 12108 | 1.56 |
| *Flavobacterium meningosepticum* IFO 12535 | 1.56 |

What is claimed is:
1. Exo-3',4'-O-benzylidene-3''-dimethylchartreusin.
2. Salts of Exo-3',4'-O-benzylidene-3''-demethylchartreusin.
3. 3''-Demethylchartreusin or its salts.

* * * * *